United States Patent [19]

Audell

[11] Patent Number: 4,800,873
[45] Date of Patent: Jan. 31, 1989

[54] METHOD FOR SETTING FRACTURES

[76] Inventor: Robert A. Audell, 10660 Rochester Ave., Westwood Village, Calif. 90024

[21] Appl. No.: 91,110

[22] Filed: Aug. 31, 1987

[51] Int. Cl.$^4$ .................................................. A61F 5/04
[52] U.S. Cl. ............................... 128/92 R; 128/92 Y; 128/92 V
[58] Field of Search ........... 128/92 Y, 92 YZ, 92 YY, 128/92 YK, 92 YE, 92 YV, 92 YT, 92 YW, 92 YS, 92 V

[56] References Cited

U.S. PATENT DOCUMENTS

| | | | |
|---|---|---|---|
| 2,518,019 | 8/1950 | Kane | 128/92 YZ |
| 2,934,065 | 4/1960 | Townley | 128/92 A |
| 2,985,168 | 5/1961 | Jonas et al. | 128/83 |
| 3,208,450 | 9/1965 | Abelson | 128/92 YZ X |
| 3,334,624 | 8/1967 | Schneider et al. | 128/92 YZ |
| 3,717,146 | 2/1973 | Halloran | 128/92 YZ |
| 3,867,932 | 2/1975 | Huene | 128/92 E |
| 3,977,398 | 8/1976 | Burstein | 128/92 BC |
| 4,237,875 | 12/1980 | Termanini | 128/92 BA |
| 4,432,358 | 2/1984 | Fixel | 128/92 V X |
| 4,498,468 | 2/1985 | Hansson | 128/92 YK |
| 4,528,980 | 7/1985 | Kenna | 128/92 EB |
| 4,541,424 | 9/1985 | Grosse et al. | 128/92 EB |
| 4,558,697 | 12/1985 | Wu | 128/303 R |
| 4,574,794 | 3/1986 | Cooke et al. | 128/92 H |
| 4,616,638 | 10/1986 | Griggs | 128/92 YV |
| 4,621,628 | 11/1986 | Brudermann | 128/92 UD |
| 4,622,959 | 11/1986 | Marcus | 128/92 YZ |

OTHER PUBLICATIONS

Journal of Bone & Joint Surgery, Richards Manf. Co. Advertisement, Hanson-Street Intramedullary Nail, vol. 33A, Apr. 1951, p. 21.
Campbells's Textbook of Operative Orthopaedics, pp. 597-606.

Primary Examiner—Robert A. Hafer
Assistant Examiner—Kevin G. Rooney
Attorney, Agent, or Firm—Louis L. Dachs

[57] ABSTRACT

The invention is a method and tool used for the setting of fractured bones. In detail, the tool comprises an elongated, cylindrical rod having an axial bore. A T-shaped handle is removably fixed to one end of the rod to permit manual manipulation thereof. In the setting procedure the elongated rod is inserted into the medullary canal after it has been reamed. Manual manipulation of the rod aligns the fragments of the bone. After the bone fragments have been aligned a guide wire is passed through the bore of the rod and the rod is removed leaving the guide wire across the fracture.

5 Claims, 2 Drawing Sheets

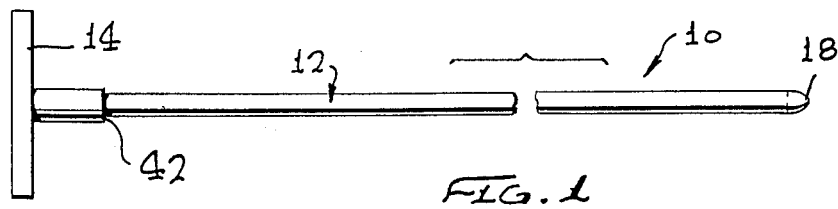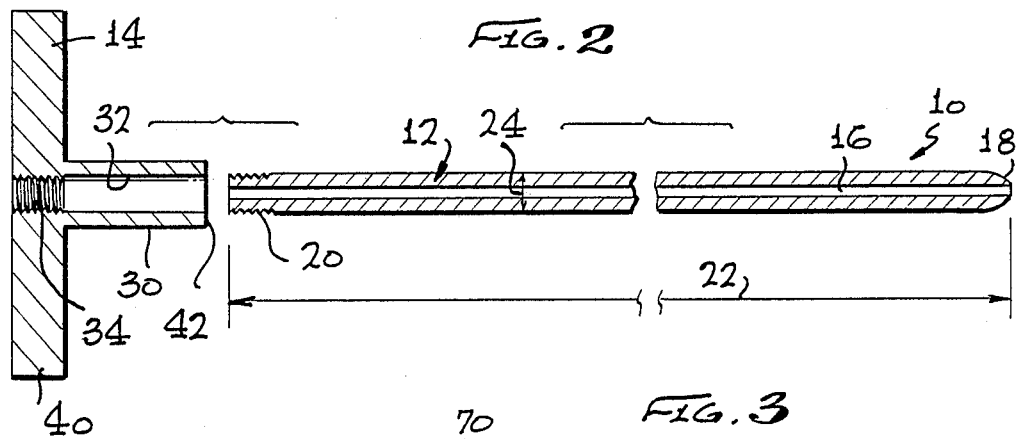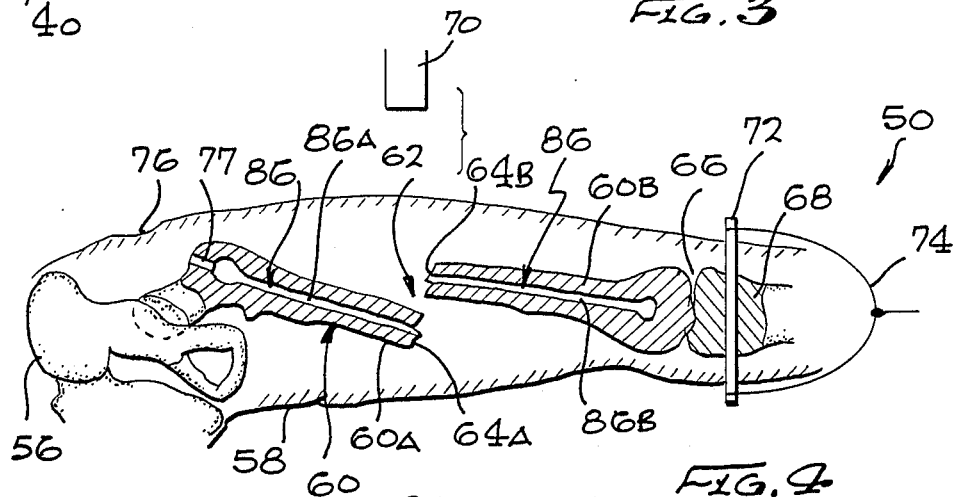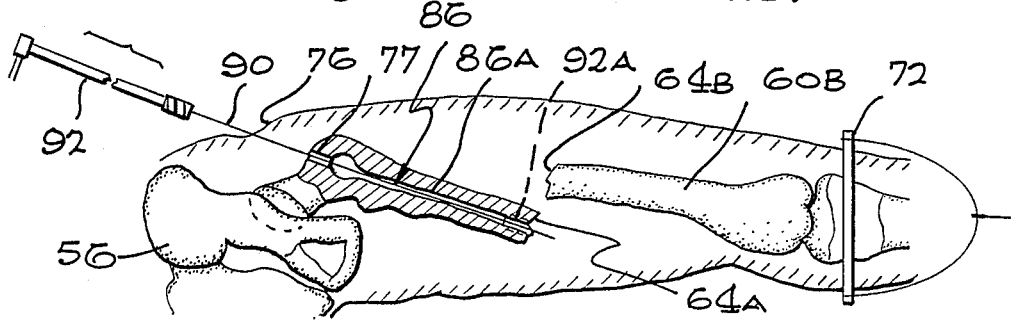

METHOD FOR SETTING FRACTURES

TECHNICAL FIELD

This invention relates to the field of methods and tools for setting fractures and, more particularly to, an improved method and tools for setting fractures by the closed medullary nailing procedure.

BACKGROUND INFORMATION

The nailing of shaft fractures of long bones without exposure of the fracture site was first advocated by Dr. Kuntscher in the 1940's. With the development of image intensifier television fluoroscopy, which reduces the amount of radiation necessary during the procedure, has led to wide acceptance of the closed nailing method. The typical procedure as presently practiced, and as particularly used for the femur bone in the thigh is as follows:

(1) The patient is positioned on a fracture table in a lateral position.

(2) A tibial traction pin is inserted.

(3) A traction force is placed across the tibial pin.

(4) Fluoroscopy is used to visualize the fracture site and to insure that the femur is out to length—i.e., the fracture ends are not overlapping.

(5) An awl is used to enter the medullary canal in the upper part of the femur (near the hip).

(6) A flexible guide wire is inserted and advanced to the fracture site.

(7) External pressure is applied to the exterior of the thigh to force the portions of the femur into alignment using fluoroscopy to guide the physician. Typically, this is accomplished by use of an unsterilized crutch or the like. An alternate approach is disclosed in U.S. Pat. No. 4,558,697 "Method and Apparatus for Setting Fractures" by K. K. Wu. Here, a pair of hook like members are used to externally manipulate the thigh while the fracture site is under X-ray. These hooks have a sufficient length such that handles at the opposite end can be used for manipulating the hook ends from a point out of the exposure range of the X-ray. These hooks have the additional advantage of being easily sterilized.

(8) The guide wire is thereafter advanced across the fracture site of the aligned segments of the femur to the end thereof.

(9) A reamer is inserted and the canal is reamed its entire length—i.e. the reamer has a central hole through which the wire extends and is guided thereby.

(10) Thereafter, the reamer is removed and the nail is inserted into the reamed hole, again using the wire as a guide.

(11) The guide wire is thereafter removed and the surface opening closed.

The main advantage of the closed nailing procedure is obvious, i.e., the fracture site is not exposed. However, the above procedure is not without problems for it is often difficult to align segments of the broken bone by use of only external manipulation. Often exposure of the fracture site to visualize and obtain proper alignment is required.

Thus, it is a primary object of the subject invention to provide a method and tool for setting fractures which eliminates the need for direct exposure of the fracture site.

It is another object of the subject invention to provide a method and tool for closed nailing of fractured bones that can achieve alignment of the fractured bone portions without external manipulation of the limb or at least greatly reducing the need for such external manipulation.

DISCLOSURE OF THE INVENTION

The invention is a method for setting fractured, long, hollow bones of a limb, while the limb is under at least periodic X-ray observation and a tool to aid in this method. The method comprises the following steps:

1. Placing the limb in traction;

2. Making an opening from the exterior of the limb to the medullary canal of the bone through one end thereof;

3. Inserting a guide wire through the opening into the medullary canal to the fracture site;

4. Reaming the medullary canal to the point of fracture by means of a hollow reamer guided by the wire;

5. Removing the reamer and the guide wire from the canal;

6. Inserting an aligning tool in the reamed canal through the opening to the point of the fracture. The aligning tool includes an elongated, cylindrical rod having an axial bore therethrough. The rod has a length sufficiently long so as to reach the point of fracture from a point external of the limb (from the opening) and a diameter only just slightly smaller than the diameter of the reamer used to ream the canal A handle is mounted to one end for gripping purposes.

7. The tool is leveraged to align the reamed portion of the bone so it becomes aligned with the unreamed portion using the X-ray exposures as a guide;

8. After the reamed and unreamed portion of the bone are aligned a guide wire is inserted through the tool, through the reamed portion, across the fracture site and to the opposite end of the unreamed portion;

9. Thereafter the aligning tool is removed;

10. The reamer is then reinstalled and the second portion of the bone is reamed, again using the wire as a guide;

11. The reamer is then removed;

12. A hollow nail is then installed into the totally reamed and aligned canal; and 13. Finally, the guide wire is withdrawn and the opening closed.

The novel features which are believed to be characteristic of the invention, both as to its organization and method of operation, together with further objects and advantages thereof, will be better understood from the following description in connection with the accompanying drawings in which the presently preferred embodiment of the invention is illustrated by way of example. It is to be expressly understood, however, that the drawings are for purposes of illustration and description only and are not intended as a definition of the limits of the invention.

BRIEF DESCRIPTION OF THE DRAWINGS

Illustrated in FIG. 1 is a side elevation view of the tool used for aligning the portions of the fractured bone prior to nailing.

Illustrated in FIG. 2 is an exploded cross-sectional view of the tool shown in FIG. 1.

Illustrated in FIG. 3 is a partial schematic representation of a portion of a patient, in particular the thigh area with the femur bone fractured.

Illustrated in FIG. 4 is a partial schematic representation of the thigh area shown in FIG. 3 illustrating the method used to ream the medullary canal of the fractured femur.

Figure 5:
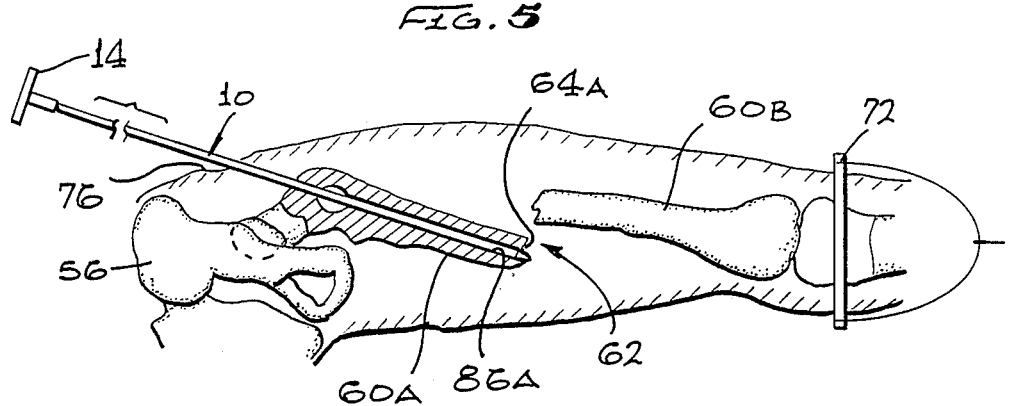

Illustrated in FIG. 5 is a partial schematic representation of the thigh area shown in FIG. 4 illustrating the insertion of the alignment tool into the reamed portion of the medullary canal of the femur.

Figure 6:
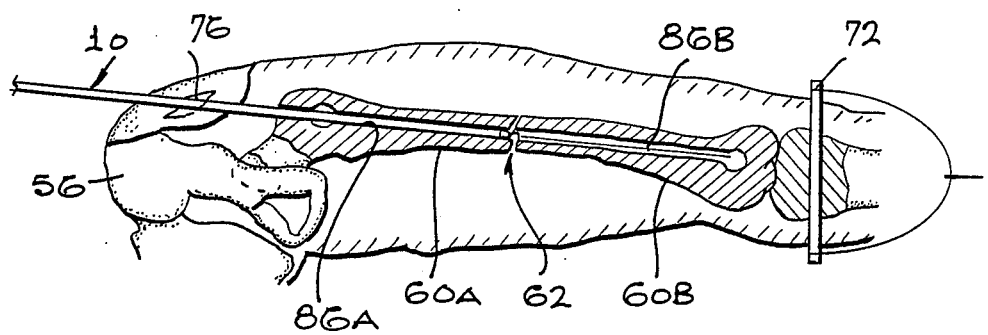

Illustrated in FIG. 6 is a partial schematic representation of the thigh area shown in FIG. 5 illustrating the use of the alignment tool to align the fractured portions of the femur bone.

Figure 7:
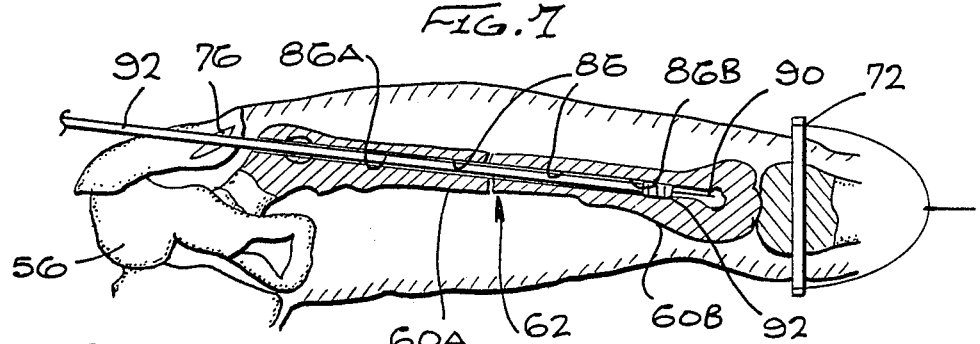

Illustrated in FIG. 7 is a partial schematic representation of the thigh area shown in FIG. 6 illustrating the step of reaming the second portion of the fractured femur.

Figure 8:
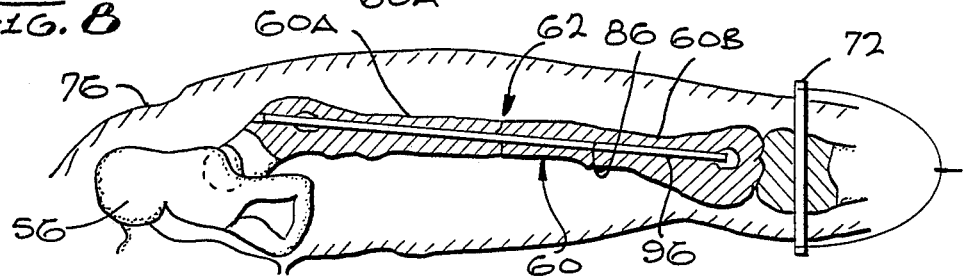

Illustrated in FIG. 8 is a partial schematic representation of the thigh area shown in FIG. 7. Illustrating the step of nailing the reamed and aligned femur.

BEST MODE FOR CARRYING OUT THE INVENTION

Illustrated in FIG. 1 is a side elevation view of the alignment tool, while illustrated in FIG. 2 is an exploded cross-sectional view of the tool shown in FIG. 1. The tool, generally indicated by numeral 10, comprises an elongated, cylindrical rod 12 with a T-shaped handle 14 attached at one end. The rod 12 has an internal bore 16 extending completely therethrough with a pointed first end 18 and an externally threaded second end 20. The overall length and diameter, indicated by numeral 22 and 24, respectively, are important and the required dimensions thereof will be subsequently discussed. The T-shaped handle 14 comprises a shaft portion 30 with an internal bore 32 sized to slidably mate with the rod 12. The shaft portion 30 includes a threaded end 34 adapted to receive threaded end 20 of the rod 12. A crossbar, indicated by numeral 40 is, typically, welded onto the shaft.

This particular design configuration of having the threaded end 20 of the rod 12 engaging threads 34 of the shaft portion 30 eliminates stress concentrations that would occur if the rod threadably engaged the shaft portion at end 42. Furthermore, this take-apart construction provides for sterilization. The tool should be made of stainless steel or Titanium to resist corrosion or other chemical attack.

The tool is used in the subsequent method for setting fractures, particularly in the closed medullary nailing procedure for long bones without exposure of the fracture site. The example hereinbelow presented uses, for purposes of illustration, the closed medullary nailing of a fractured femur bone in the thigh of the patient with only one fracture site. It should be understood, however, that this procedure is suitable for use on fractures in the lower leg, and upper and lower arms and can also be used with multiple fractured bones.

Illustrated in FIG. 3 is a partial schematic representation of the thigh area of a patient, generally designated by numeral 50. Shown are the hip bone 56 and thigh (femur) bone 60, which for purposes of illustration only, is shown fractured at site 62 into upper portion 60A having fractured end 64A and lower portion 60B having fractured end 64B. Also illustrated is the knee joint 66 and a portion of the lower leg bone or tibia 68. As part of the procedure an X-ray (fluoroscopy) Unit 70 is used to take at least periodic pictures, as required, of the fracture site 62 to aid in the alignment of the fractured portions of the femur.

The thigh 50 is placed in traction by the insertion of a tibial traction pin 72 attached by wire 74 to a weight (not shown). The traction portion of the procedure is well-known and thus, need not be discussed in detail here. It is normally required to insure that the ends 64A and 64B do not overlap at the fracture site 62 and placing the limb in traction will eliminate such overlap.

Still referring to FIG. 3 and additionally to FIG. 4 the procedure begins with the making of an incision indicated by numeral 76 in the thigh 58 above the femur 60 and the drilling of a hole 77 by use of an awl (not shown) into the inter medullary canal 86 (canal portion 86A). Thereafter a standard semi-flexible wire 90 (typically 3 millimeters in diameter) is inserted through the incision 76, hole 77 and portion 86A of the canal 86 to the end 64A. A standard inner medullary reamer 92 is used to ream the canal portion 86A to end 64A (indicated by dotted lines and numeral 92A) using the wire 90 as a guide. The reamer will vary in diameter but, typically for the femur of adults, a 9 millimeter diameter reamer is used. Note that the reamer has a hole therethrough (not shown) so that it can be guided down the wire. The wire 90 and reamer 92 are thereafter removed.

Now referring to FIGS. 5 and 6 it can be seen that the next steps are to insert the previously described alignment tool 10 into the reamed canal portion 86A to its end 64A. The tool 10 has a rod diameter 24 (best seen in FIG. 2) only slightly smaller than the diameter of the reamer 92 such that good contact with the reamed canal wall is obtained. Thus, if a 9 millimeter reamer had been used then the rod diameter should ideally be between 8.5 to 8.9 millimeter. The length 22 of the rod must be sufficiently long so as to reach the fracture site 62 while still allowing external manipulation of the tool. Here, the X-ray machine 70 comes into critical use. Thereafter, the portion 60A is aligned with the portion 60B (the ends 64A and 64B in aligned contact by manipulation of the tool 10, by means of the handle 14. Some variation in traction force may be necessary to achieve alignment. While in most cases external manipulation is unnecessary to achieve alignment, it is sometimes necessary to apply an external force. This can be accomplished by use of the previously mentioned crutch (not shown), or the hooks as disclosed in U.S. Pat. No. 4,558,657. The guide wire 90 is introduced into hole 16 of the tool, across the aligned ends 64A and 64B and into the end of the canal portion 86B of the aligned femur portion 60B. Thereafter the alignment tool 10 is removed.

Referring to FIG. 7 it can be seen that the reamer 92 is then used to ream the reamed canal portion 86B to its end again using the wire 90 as a guide. The reamer 92 is then removed, however, the wire 90 is left in place. Finally referring to FIG. 8 the next step is to install the nail, indicated by numeral 96, into the now fully reamed canal 86. The nail of course has a hole therethrough and the wire 90 is again used as a guide. The guide wire 90 is then removed and the incision closed.

The use of the above procedure has several important advantages:

(1) The alignment of the fractured portion can usually be accomplished without the need for external manipulation.

(2) The use of the tool designed to fit into the reamed portion of the canal provides an excellent fit and thus, efficient load transfer into the portion of the fractured bone being aligned making such alignment easy to accomplish. An attempt to use the guide wire to move the fractured portions into alignment is not effective since the wire is flexible. The use of an undersized nail in a non-reamed hole can lead to the nail becoming stuck since the canal walls are highly irregular in cross-section.

While the invention has been described with reference to a particular embodiment, it should be understood that the embodiment is merely illustrative as there are numerous variations and modifications which may be made by those skilled in the art. Thus, the invention is to be construed as being limited only by the spirit and scope of the appended claims.

INDUSTRIAL APPLICABILITY

The invention has applicability in the closed nailing procedure for setting fractures of long bones.

I claim:

1. A method of setting fractured long bones, having a central medullary canal, of a limb while the limb is under at least periodic X-ray observation comprising the steps of:
   placing the limb in traction;
   making an opening from the exterior of the limb to the intermedullary canal of the bone through one end thereof;
   inserting a guide wire through said opening into the canal at the point of fracture;
   reaming the canal to the point of fracture by means of a hollow reamer guided by said wire;
   removing said reamer and said guide wire from the limb;
   inserting an aligning tool in said reamed portion of the canal through said aligned opening to the point of the fracture, said aligning tool having a passageway therethrough;
   leveraging said tool to align the reamed portion of the bone with the unreamed portion of the bone using X-ray exposures as a guide;
   inserting a second guide wire through said reamed portion and the remaining unreamed portion of the bone;
   reaming the second portion of the bone by means of said hollower reamer guided by said second guide wire;
   removing said reamer;
   installing a hollow pin in said aligned canal; and
   withdrawing said second guide wire.

2. The tool as set forth in claim 1, wherein the opposite end of said rod is pointed.

3. The method as set forth in claim 1 where said tool comprises:
   an elongated, cylindrical rod having an axial bore therethrough, said rod having a diameter only just sufficiently smaller than the diameter of the reamer used to ream the hole; and
   a handle means mounted to one end of said rod.

4. The method as set forth in claim 3, including said rod having a length sufficiently long so as to reach the point of fracture from a point external of the limb.

5. The method as set forth in claim 4 wherein said tool further comprises:
   said opposite end of said rod is externally threaded; and
   said handle means comprising;
   a shaft having first and second ends and an internal bore therethrough, said second end having internal threads adapted to receive said threaded one end of said rod portion when inserted from said first end thereof; and
   a handle comprising a bar mounted at its middle portion to said second end of said shaft at right angles thereto.

* * * * *